United States Patent [19]

Pruna

[11] Patent Number: 5,532,239
[45] Date of Patent: Jul. 2, 1996

[54] THERAPEUTIC APPLICATION OF FLUOROQUINOLONE DERIVATIVES

[75] Inventor: André Pruna, Paris, France

[73] Assignee: Assistance Publique - Hopitaux de Paris, Paris, France

[21] Appl. No.: 100,799

[22] Filed: Aug. 2, 1993

[51] Int. Cl.$^6$ .................................................. A61K 31/495
[52] U.S. Cl. ................................................................ 514/254
[58] Field of Search ........................................ 514/253, 254

[56] References Cited

U.S. PATENT DOCUMENTS

| | | | |
|---|---|---|---|
| 4,448,962 | 5/1984 | Irikura et al. | 544/362 |
| 4,499,091 | 2/1985 | Wentland et al. | 514/254 |
| 4,668,784 | 5/1987 | Mascellani et al. | 544/32 |
| 4,704,459 | 11/1987 | Todo et al. | 546/123 |
| 4,795,751 | 1/1989 | Matsumoto et al. | 514/254 |

FOREIGN PATENT DOCUMENTS

| | | |
|---|---|---|
| 870576 | 3/1979 | Belgium . |
| 887574 | 6/1981 | Belgium . |
| 0047005 | 3/1982 | European Pat. Off. . |
| 0078362 | 5/1983 | European Pat. Off. . |
| 0131839 | 7/1984 | European Pat. Off. . |
| 0140116 | 5/1985 | European Pat. Off. . |
| 0154780 | 9/1985 | European Pat. Off. . |
| 0206283 | 12/1986 | European Pat. Off. . |
| 0221463 | 5/1987 | European Pat. Off. . |
| 0310849 | 4/1989 | European Pat. Off. . |
| 0520240 | 12/1992 | European Pat. Off. . |
| 3142854 | 5/1983 | Germany . |

OTHER PUBLICATIONS

The Merck Manual, 14th Edition (1982) pp. 1544–1549.
The Lancet "Perfloxacin as first–line treatment in Nephrotic syndrome", vol. 340: Sep. 19, 1992, A. Pruna et al.
Le Quotidien du Medecin "un rôle inattendu pour un antibiotique: le traitement du syndrome néphrotique" Sep. 21, 1992, Dr. De Viel.
"Conventional Therapy for Idiopathic Nephrotic Syndrome in Children", J. Brodehl, *Clinical Nephrology*, vol. 35, Suppl. 1, pp. S8–15, 1991.

*Primary Examiner*—Raymond Henley, III
*Attorney, Agent, or Firm*—Spencer & Frank

[57] ABSTRACT

This invention relates to treatment or prevention of nephrotic syndromes by administration of a derivative of the fluoroquinolone class corresponding to the general formula:

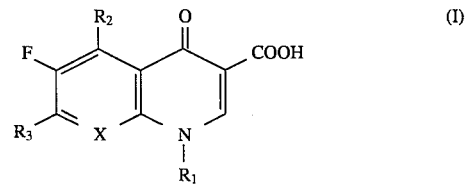

in which: $R_1$ is an alkyl (1 to 4 carbon atoms), fluoroethyl, cyclopropyl, methylamino or difluorophenyl radical, X represents a nitrogen atom or a group $=CRT_7-$ in which $R_7$ is H, Cl or F or alternatively $R_7$ forms, with the $R_1$ radical and the atoms to which they are attached, a six-membered heterocycle substituted by methyl and optionally containing an oxygen or sulphur atom, $R_2$ is H, or can represent an amino radical, if $R_7$ is F, and $R_3$ is H, a 2,8-diazabicyclo [4.3.0]non-8-yl radical or a radical of structure:

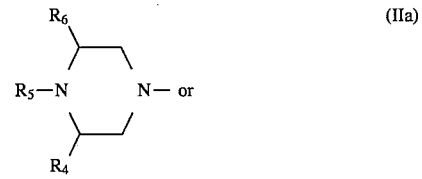

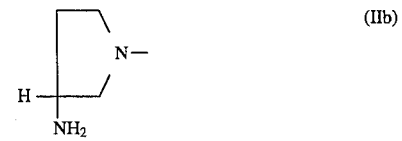

in which $R_4$, $R_5$ and $R_6$ are identical or different and represent H or methyl, or one of its pharmaceutically acceptable salts.

4 Claims, No Drawings

THERAPEUTIC APPLICATION OF FLUOROQUINOLONE DERIVATIVES

FIELD OF THE INVENTION

The present invention relates to a new therapeutic application of fluoroquinolone derivatives for the treatment of nephrotic syndromes.

BACKGROUND OF THE INVENTION

Nephrotic syndrome is a serious kidney ailment, characterized by a hypoalbuminemia and by a significant proteinuria (mainly albuminuria) as well as by the appearance of an oedematous syndrome. It sometimes results in requiring extra-renal purification, kidney transplantation or can even be responsible for fatal complications, in particular in infants.

Nephrotic syndrome is usually treated by corticotherapy or by means of medicaments such as azathioprine, cyclosporin A or chlorambucil. These long-lasting treatments (an average of 6 months to one year) can be accompanied by harmful side-effects of the corticosteroids or lead to toxic effects of haematological, hepatic, gonadal or renal nature. Recurrences are frequent and justify the prescription of repeated and sustained treatments. Moreover, a certain number of nephrotic syndromes are resistant to any treatment. Many cases develop towards extra-renal complications and towards chronic renal insufficiency.

The therapeutic class of the fluoroquinolones is widely known and used in antibacterial treatments. The references below describe the derivatives used according to the invention, as antibacterial agents:
BE 870,576, U.S. Pat. No. 4,448,962, DE 3,142,854, EP 047,005, EP 206,283, BE 887,574, EP 221,463, EP 140,116, EP 131,839, EP 154,780, EP 078,362, EP 310,849, EP 520,240, U.S. Pat. No. 4,499,091, U.S. Pat. No. 4,704,459, U.S. Pat. No. 4,795,751, U.S. Pat. No. 4,668,784.

DESCRIPTION OF THE INVENTION

It has now been found that the products of the fluoroquinolone class, corresponding to the general formula:

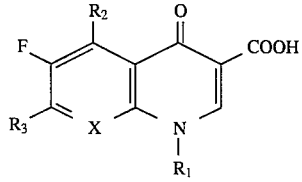

in which $R_1$ is an alkyl, containing 1 to 4 carbon atoms, fluoroethyl, cyclopropyl, methylamino or difluorophenyl radical, X represents a nitrogen atom or a group $=CR_7-$ which $R_7$ is a hydrogen, chlorine or fluorine atom or alternatively $R_7$ forms, with the $R_1$ radical and the atoms to which they are attached, a six-membered heterocycle substituted by a methyl radical and optionally containing an oxygen or sulphur atom, $R_2$ is a hydrogen atom, or can represent an amino radical, if $R_7$ is a fluorine atom, and $R_3$ is a hydrogen atom, a 2,8-diazabicyclo[4.3.0]non-8-yl radical or a radical of structure:

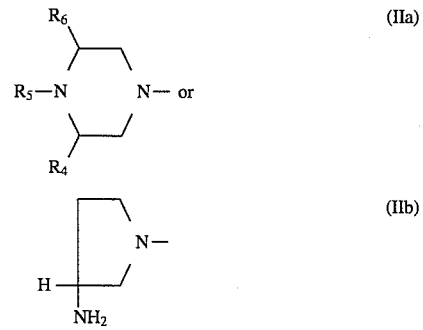

in which $R_4$, $R_5$ and $R_6$ are identical or different and represent hydrogen atoms or methyl radicals, or their pharmaceutically acceptable salts, surprisingly show an effect on nephrotic syndrome and thus make it possible to obtain remission of and recovery from this illness.

Among the quinolones mentioned above, the following are more especially advantageous: pefloxacin, sparfloxacin, ciprofloxacin, ofloxacin, levofloxacin, enoxacin, norfloxacin, fleroxacin, lomefloxacin, temafloxacin, amifloxacin, tosufloxacin, flumequine, rufloxacin, clinafloxacin, Bay y 3118 or PD 131 628.

The activity of the products of general formula (I) was shown in the following way:

Patients suffering from nephrotic syndrome, having a proteinuria of 2.5 g to 12.5 g per 24 hours and a plasma albumin level ranging from 22 to 42 g/l at day $D_0$, receive pefloxacin [1,4-dihydro-1-ethyl-6-fluoro-7-(4-methylpiperazinyl)-4-oxoquinoline-3-carboxylic acid] at $D_1$ at a charge of 2 times 400 mg orally. The daily treatment is thus continued for 2 to weeks. Proteinuria is measured respectively at $D_{15}$ and at $D_{30}$. Albuminemia is measured at $D_{30}$. The results are summarized below in Table I.

TABLE I

| Patient No. | Proteinuria at $D_0$ g/24 hours | Plasma albumin at $D_0$ g/liters | Duration of the treatment (weeks) | Proteinuria at $D_{15}$ g/24 hours | Proteinuria at $D_{30}$ g/24 hours | Plasma albumin at $D_{30}$ g/liters | Recurrence |
|---|---|---|---|---|---|---|---|
| 1 | 7 | 41.6 | 2 | <0.20 | <0.20 | not tested | at 3 months |
| 2 | 5.5 | 28.5 | 4 | 1.64 | 0.34 | 36 | no |
| 3 | 9.7 | 22 | 4 | not tested | 1.32 | 24 | no |
| 4 | 2.8 | 26 | 4 | <0.20 | <0.20 | not tested | no |

TABLE I-continued

| Patient No. | Proteinuria at $D_0$ g/24 hours | Plasma albumin at $D_0$ g/liters | Duration of the treatment (weeks) | Proteinuria at $D_{15}$ g/24 hours | Proteinuria at $D_{30}$ g/24 hours | Plasma albumin at $D_{30}$ g/liters | Recurrence |
|---|---|---|---|---|---|---|---|
| 5 | 12 | 25 | 4 | 0.35 | 0.54 | 33 | at 2 months |
| 6 | 6.5 | not tested | 5 | 1.17 | 0.20 | 28 | no |
| 7 | 7 | 26 | 2 | 1.82 | 0.60 | 35.3 | at 6 months |
| 8 | 12.5 | 24 | 4 | 9 | 1.75 | 23.6 | — |

In their entirety, the results show that remission is obtained between the 8th and fifteenth day of treatment, when proteinuria is observed to vanish over a period of 3 days.

The patients who have suffered recurrence are again treated with 2 times 400 mg per day of pefloxacin. The results are summarized in Table II below:

TABLE II

| Patient No. | Duration of treatment (weeks) | Result |
|---|---|---|
| 1 | 4 | Remission |
| 5 | 4 | Remission |
| 7 | 4 | Remission |

Recession without recurrence and without treatment is 4 years for the first patient treated (not shown in Table I). A recession of 12 months is observed in a patient treated after a 2nd recurrence (patient No. 1). A patient (No. 7), having received a kidney transplant and having shown a recurrence of nephrotic syndrome with minor glomerular lesions (NS-MGL) from $D_3$, was treated for 15 days from $D_{17}$ post-transplant with pefloxacin, and then for 1 month after the 7th month post-transplant; a recession without recurrence of 1 year and 3 months is observed with a proteinuria varying from 0.4 to 0.6 g/24 hours.

In such a protocol, the other fluoroquinolones of general formula (I) show analogous results.

The present invention relates to a medicament intended for the treatment of nephrotic syndromes, containing at least one product of general formula (I), optionally in the salt form, in the pure state or in the form of a pharmaceutical composition in combination with one or a number of compatible and pharmaceutically acceptable diluents and/or adjuvants.

These compositions can be administered orally or parenterally.

As solid compositions for oral administration, there can be used tablets, pills, gelatin capsules, powders or granules. In these compositions, the active product according to the invention is mixed with one or a number of inert diluents or adjuvants, such as sucrose, lactose or starch. These compositions can comprise substances other than the diluents, for example a lubricating agent such as magnesium stearate.

As liquid compositions for oral administration, there can be used pharmaceutically acceptable solutions, suspensions, emulsions, syrups and elixirs containing inert diluents such as water or paraffin oil. These compositions can also comprise substances other than the diluents, for example wetting, sweetening or flavoring substances.

The compositions for parenteral administration can be aqueous or non-aqueous sterile solutions, suspensions or emulsions. As solvent or vehicle, it is possible to use propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by irradiation or by heating. They can also be prepared in the form of sterile solid compositions which can be dissolved at the time of use in sterile water or any other injectable sterile medium.

The compositions comprising fluoroquinolone derivatives can be administered curatively or preventively in subjects showing cases of nephrotic syndrome, such as, for example, idiopathic nephrotic syndrome with minor glomerular lesions, extra-membranous glomerulonephrites or idiopathic membranoproliferative glomerulonephrites.

According to the invention, the doctor will determine the dose which he judges the most suitable according to a preventive or curative treatment, according to the age, weight, extent of the syndrome and other factors specific to the subject to be treated.

By way of example, it can be between 400 mg, 3 times per week and a daily dose of 800 mg for 15 days to 1 month. Nevertheless, if appropriate, the daily doses could be higher, daily doses of 5 g in adults being acceptable.

EXAMPLES

The following examples illustrate compositions according to the invention intended for the treatment of nephrotic syndrome:

EXAMPLE

Tablets containing a dose of 400 mg are prepared which have the following composition:

Pefloxacin in the mesylate dihydrate form: 400 mg
Excipient:
  core: wheat starch, gelatin, talc, magnesium stearate, sodium carboxymethylstarch q.s. for a core;
  coating: hydroxypropyl methylcellulose, ethyl cellulose, dibutyl sebacate, titanium oxide, talc, polyethylene glycol 6000.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. A method for the treatment of nephrotic syndromes with minor glomerular lesions comprising administering to a host in need thereof a derivative of the fluoroquinolone class corresponding to the formula:

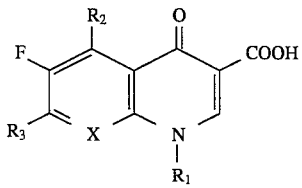

in which $R_1$ is an alkyl, containing 1 to 4 carbon atoms, fluoroethyl, cyclopropyl, methylamino or difluorophenyl radical, X represents a nitrogen atom or a group $=CR_7-$ in which $R_7$ is a hydrogen, chlorine or fluorine atom or alternatively $R_7$ forms, with the $R_1$ radical and the atoms to which they are attached, a six-membered heterocycle substituted by a methyl radical and optionally containing an oxygen or sulphur atom, $R_2$ is a hydrogen atom, or can represent an amino radical, if $R_7$ is a fluorine atom, and $R_3$ is a hydrogen atom, a 2,8-diazabicyclo[4.3.0]non-8-yl radical or a radical of structure:

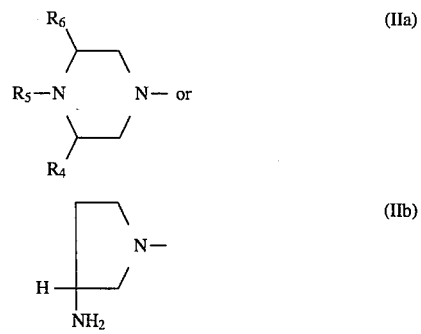

in which $R_4$, $R_5$ and $R_6$ are identical or different and represent hydrogen atoms or methyl radicals, or one of its pharmaceutically acceptable salts.

2. A method according to claim 1, for the treatment of nephrotic syndromes with minor glomerular lesions, wherein there is administered to a host in need thereof a product belonging to the fluoroquinolone class selected from the group consisting of pefloxacin, sparfloxacin, ciprofloxacin, ofloxacin, levofloxacin, enoxacin, norfloxacin, fleroxacin, lomefloxacin, temafloxacin, amifloxacin, tosufloxacin, flumequine, rufloxacin, clinafloxacin, Bay y 3118, or PD 131 628 or one of its pharmaceutically acceptable salts.

3. A method for the treatment of nephrotic syndromes with minor glomerular lesions, comprising administering to a host in need thereof an effective amount of pefloxacin or a pharmaceutically acceptable salt thereof.

4. A method for the treatment of nephrotic syndromes with minor glomerular lesions, comprising administering to a host in need thereof an effective amount of sparfloxacin or a pharmaceutically acceptable salt thereof.

* * * * *